United States Patent
Ellion et al.

[11] Patent Number: 6,030,215
[45] Date of Patent: Feb. 29, 2000

[54] HAND-HELD SELF-CONTAINED ORAL IRRIGATION DEVICE

[76] Inventors: M. Edmund Ellion, 3660 Woodstock Rd., Santa Ynez, Calif. 93460; Mark J. Shultz, 678 Alamo Pintado Rd., Solvang, Calif. 93463

[21] Appl. No.: 09/148,231

[22] Filed: Sep. 4, 1998

[51] Int. Cl.[7] .................................................. A16C 5/04
[52] U.S. Cl. .............................. 433/89; 222/95; 222/324; 222/385
[58] Field of Search .................................. 433/80, 82, 89, 433/120; 601/162; 222/95, 324, 325, 341, 383.1, 385, 389; 132/112, 116; 401/174, 180, 186

[56] References Cited

U.S. PATENT DOCUMENTS

| | | | |
|---|---|---|---|
| 593,446 | 11/1897 | True | 222/324 |
| 1,166,739 | 1/1916 | Bell | 222/324 |
| 1,484,920 | 2/1924 | Wolfe | 222/324 |
| 3,144,867 | 8/1964 | Trupp et al. . | |
| 3,580,429 | 5/1971 | Trindle | 222/325 |
| 4,098,434 | 7/1978 | Uhlig | 222/95 |
| 4,655,198 | 4/1987 | Hommann . | |
| 4,787,845 | 11/1988 | Valentine | 433/80 |
| 4,863,380 | 9/1989 | Creed | 433/89 |
| 5,086,756 | 2/1992 | Powell . | |
| 5,098,291 | 3/1992 | Curtis et al. | 433/89 |
| 5,273,428 | 12/1993 | Fischer | 433/80 |
| 5,286,192 | 2/1994 | Dixon | 433/80 |
| 5,697,784 | 12/1997 | Haefele et al. . | |
| 5,700,146 | 12/1997 | Kucar | 433/82 |

*Primary Examiner*—Todd E. Manahan
*Assistant Examiner*—Eduardo C. Robert
*Attorney, Agent, or Firm*—Hugh P. Gortler

[57] ABSTRACT

A self-contained hand-operated oral irrigation device for dispensing a pulsing stream of water or therapeutic fluid to the surfaces of the user's oral cavity. The irrigation device has the capability of lavaging at controlled values of pressure and volume of the dispensed fluid and withdrawing the fluid from user's oral cavity for convenient disposal. The irrigation device has a detachable section. Different types of discharge sections include a tooth brush, plaque removal brush and a gum stimulator having lavaging capabilities are provided.

34 Claims, 9 Drawing Sheets

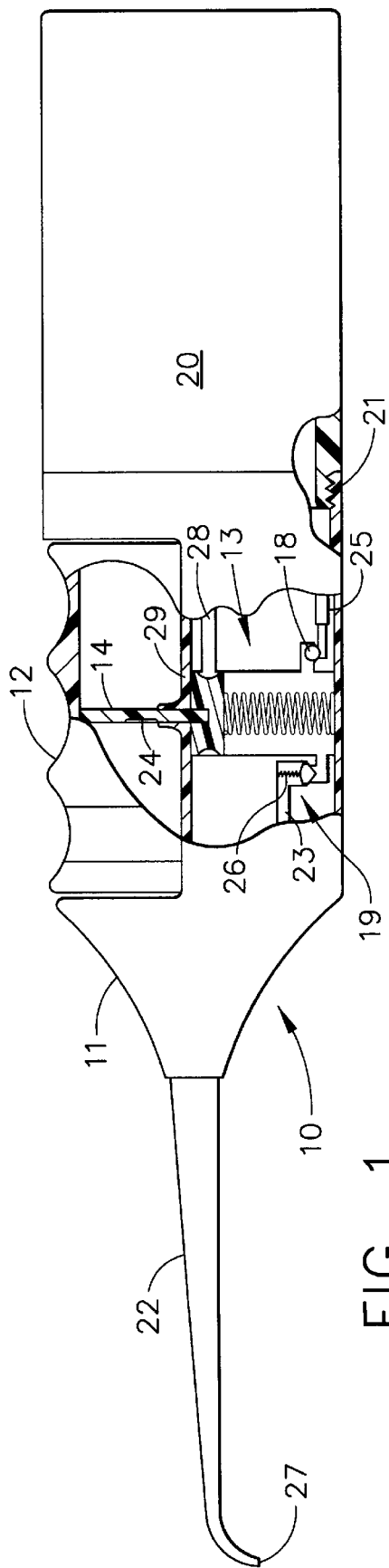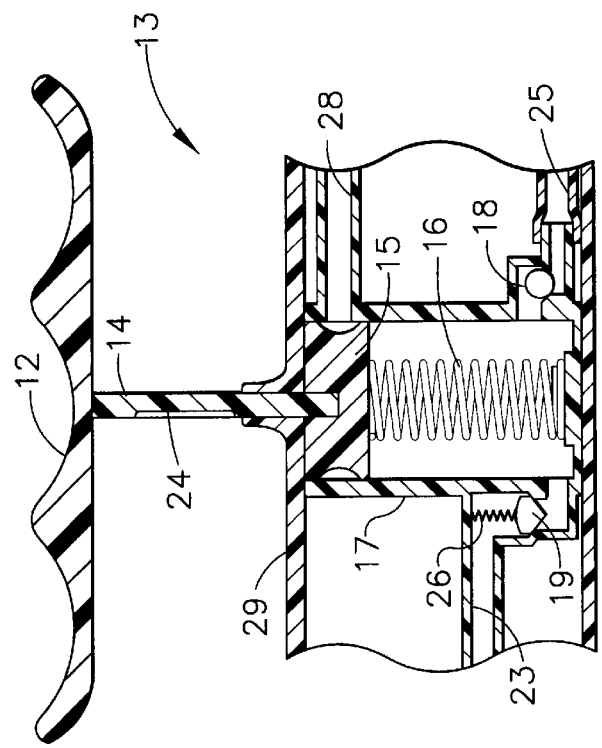
FIG. 1
FIG. 2

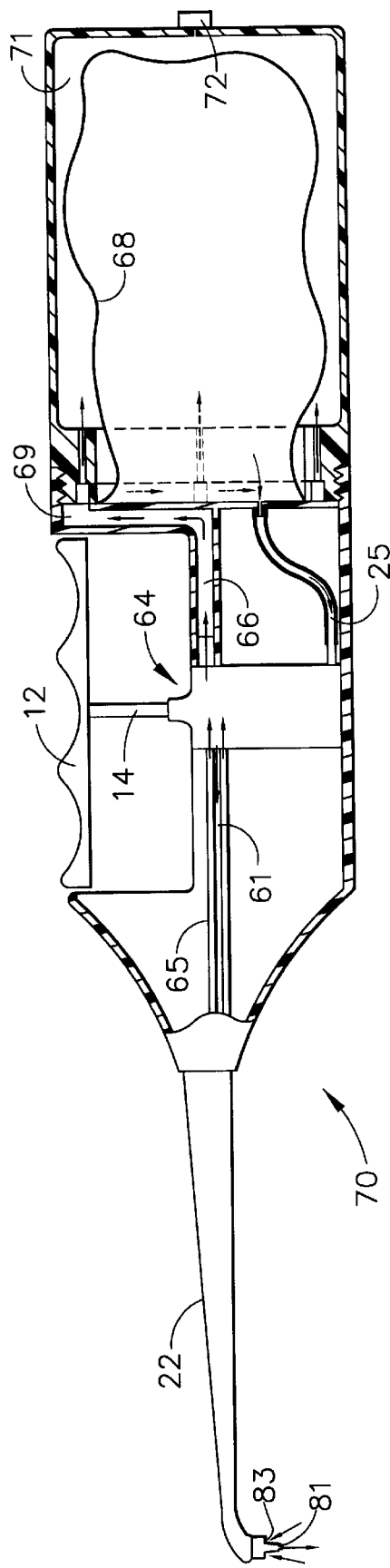
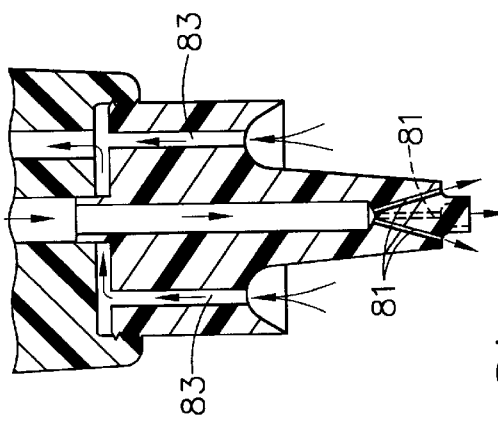
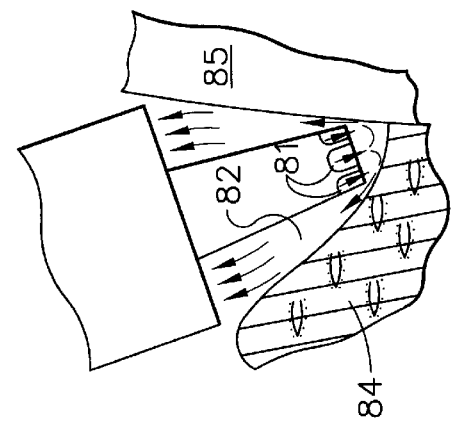
FIG. 7
FIG. 8b
FIG. 8a

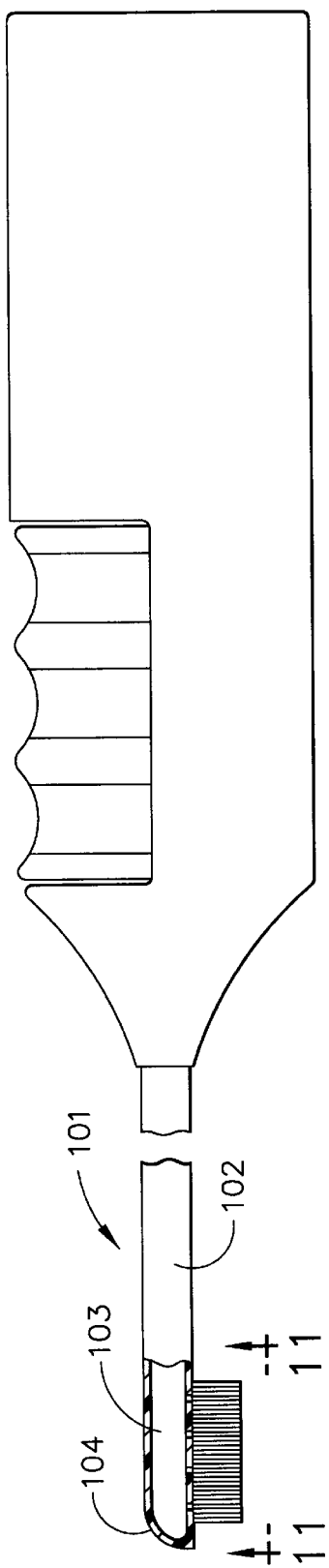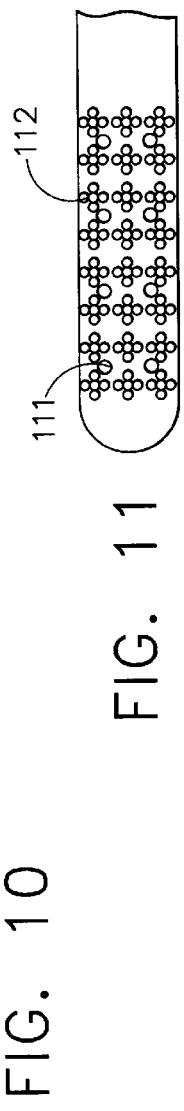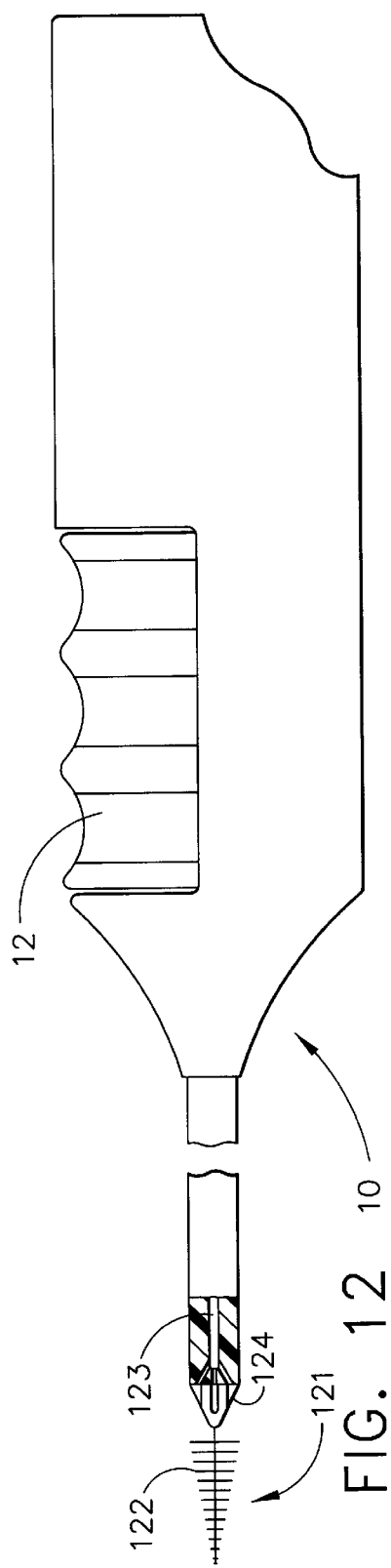
FIG. 10
FIG. 11
FIG. 12

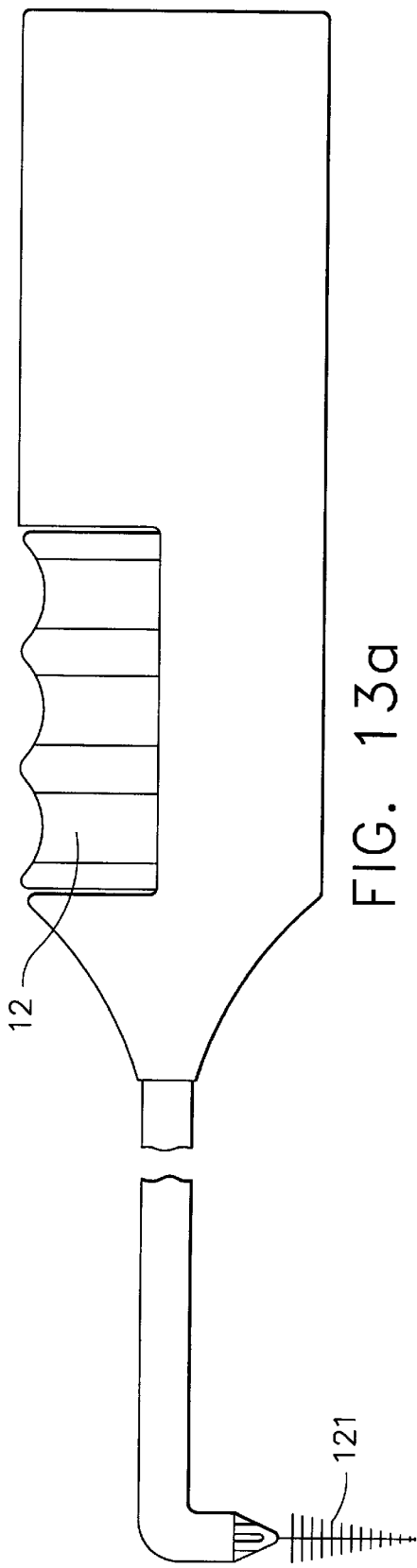
FIG. 13a
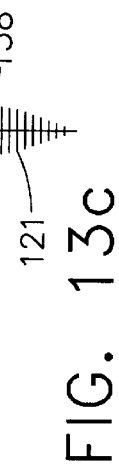
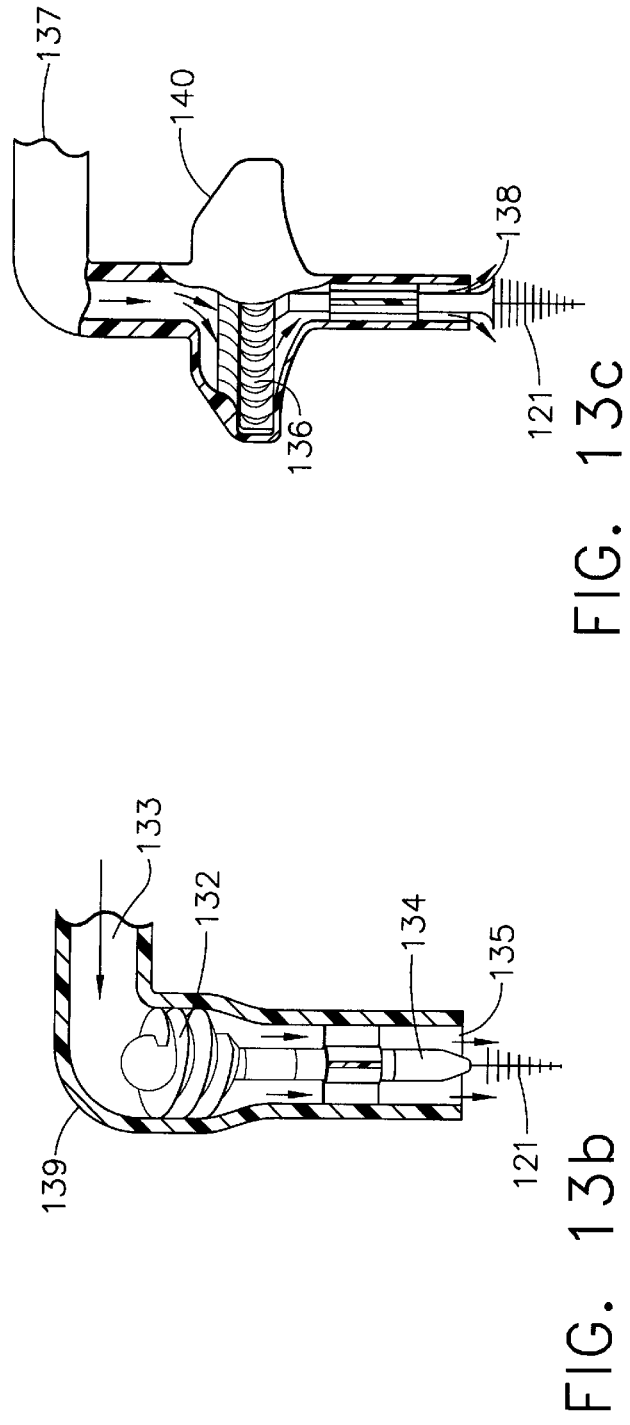
FIG. 13c
FIG. 13b

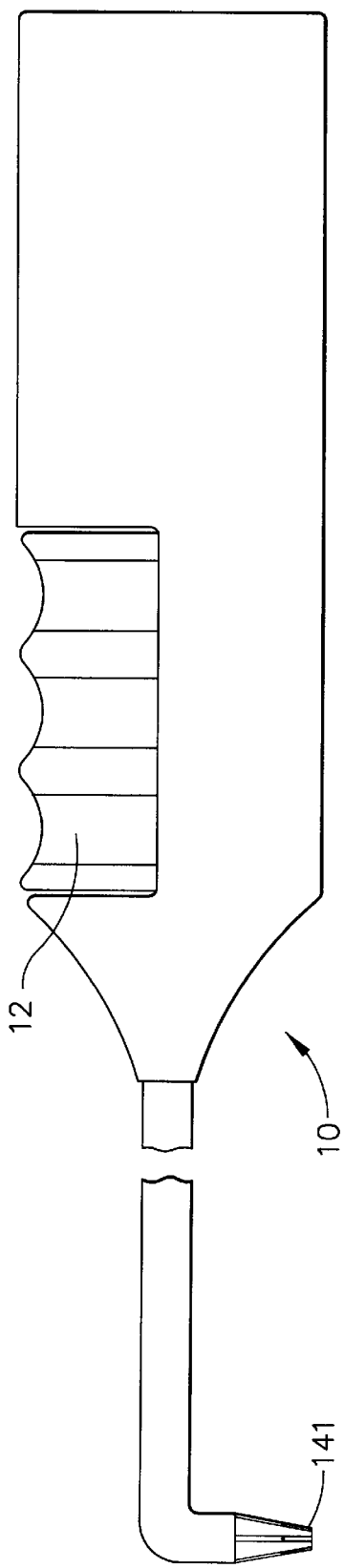
FIG. 14
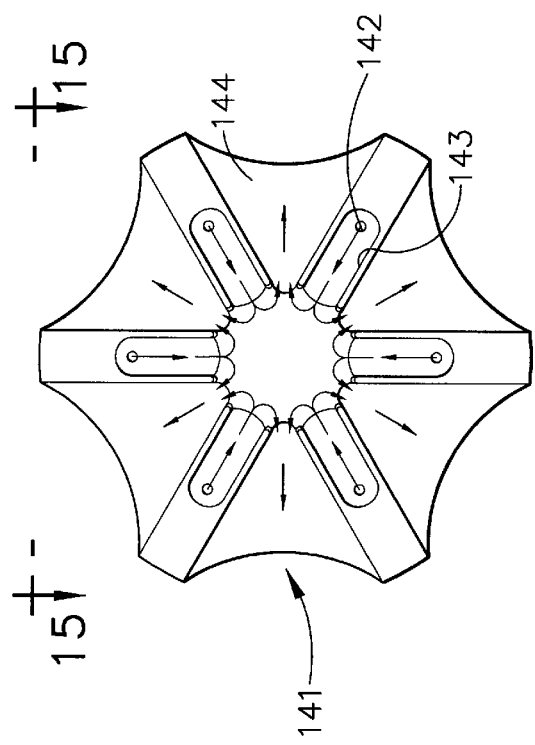
FIG. 16
FIG. 15

HAND-HELD SELF-CONTAINED ORAL IRRIGATION DEVICE

FIELD OF THE INVENTION

This invention relates generally to an oral irrigation device for delivering a stream of anti-plaque or other therapeutic liquid to lavage between teeth and around the gum line, to facilitate debridement of food particle. More particularly, the invention relates to an inexpensive self-contained hand-held oral irrigation device having a hand-operated pump.

BACKGROUND OF THE INVENTION

Over 90 percent of the adult population is infected with some form of periodontal disease. Most periodontal disease begins in the interproximal area of the mouth between the teeth. This degradation results from the bacteria that are nourished from food debris that are not removed from the gum area. Anaerobic bacterial activity in this ecological region of the gingival sulcus is the major cause of periodontal disease. As a result, it is highly desirable to remove contaminants from the gingival sulcus. Brushing will not always effectively remove the contaminants and even flossing the teeth is not completely effective. There is thus a need for a convenient oral irrigation device that will lavage between teeth and around the gum line to facilitate debridement of food particles and bacterial plague.

The most common type of oral irrigation devices includes a liquid reservoir that is positioned on a surface close to a sink and has a fluid connection tube to the exit nozzle that can reach the person's mouth. Most of these devices are powered by an electric motor. The relatively large liquid reservoir makes this type of devices awkward to transport in a suitcase for travel and the need for electrical power adds cost and limits the use in remote areas.

Another type includes the liquid reservoir and the exit nozzle housed in a hand-held self-contained package. The liquid is dispensed using either electrical power, pressurized gas or a hand-pump. The electrical power is supplied either by a battery or from a transformer. These electric or gas powered devices can be easily transported but are relatively expensive because of the electrical or gas power aspects. A further disadvantage is that the devices require replacement batteries or charged gas containers and therefore are not suitable for extended use in remote locations. In a hand operated pump, the pressure of the fluid that is discharged depends on the speed at which the pump is operated. With these hand operated pump devices, the pressure varies from a mere dribble to full pressure during the stroke resulting in ineffective use of the fluid. Other difficulties with these irrigators are that the dispensed stream often does not have sufficiently high enough pressure in order to properly clean the gum area and that they are awkward to handle.

A further important disadvantage of these irrigators is that it is difficult to dispose of the liquid that is injected into the person's mouth without soiling the wearing apparel.

There is a need for an inexpensive hand-held oral irrigation device that is completely self contained. There is a need to provide simultaneously a lavage and a vacuum to remove the dispensed fluid.

There is also a need to deliver the fluid without electrical or gas power.

There is also a need for a device that is readily portable for travel.

There is also a need for an irrigator including a hand pump that can provide an adjustable minimum liquid stream pressure that remains relatively constant while the hand-pump is operated.

There is also a need to provide an adjustable stream pulse volume.

SUMMARY OF THE INVENTION

The present invention is directed to a hand held oral irrigation device having a liquid storage reservoir, a fluid discharge section, an actuator that is movable in first and second strokes and a hand-pump. The hand-pump includes a fluid chamber having an inlet and an outlet, the chamber being in fluid communication with the fluid discharge section. The hand-pump pump has a means that is responsive to the actuator for simultaneously creating suction in the fluid chamber, opening the chamber inlet and closing the chamber outlet during the first stroke of the actuator. The means also simultaneously pressurizes the fluid chamber, closing the chamber inlet and opening the chamber outlet during the second stroke of the actuator.

BRIEF DESCRIPTION OF THE DRAWINGS

FIG. 1 is a side elevational view in a section of a first irrigator according to the present invention.

FIG. 2 is a sectional view of a hand-pump for the first irrigator.

FIG. 7 is a sectional side elevational view of the third hand-pump having the lavage and vacuum capabilities installed in the third irrigator in partial cross-section to illustrate the supply to the pump from the interior of a bladder and the discharge from the third pump to the exterior of the bladder.

FIG. 8 (a) illustrates in pictorial form, the discharge of fresh fluid and suction of used fluid in a periodontal pocket.

FIG. 8 (b) is a cross-sectional view of the lavage and suction ports in the irrigator nozzle tip.

FIG. 10 illustrates a toothbrush in place of the irrigator nozzle in a fourth irrigator according to this invention.

FIG. 11 is a plan view showing the bristles and fluid exit ports of a toothbrush.

FIG. 12 illustrates a plaque removal brush installed in an irrigator in a longitudinal orientation.

FIG. 13 (a) illustrates the plaque removal brush installed in the irrigator in a right angle orientation.

FIG. 13 (b) illustrates the plaque removal brush with a simple liquid screw device that causes the brush to rotate when driven by the fluid from the reservoir.

FIG. 13 (c) illustrates the plaque removal brush with a liquid turbine that causes the brush to rotate when driven by the fluid from reservoir.

FIG. 14 illustrates a gum massaging/stimulator tip installed in an irrigator.

FIG. 15 is an enlarged side view of the gum massaging tip.

FIG. 16 is an end view of the gum massaging tip.

DETAILED DESCRIPTION OF THE INVENTION

Figure 3:
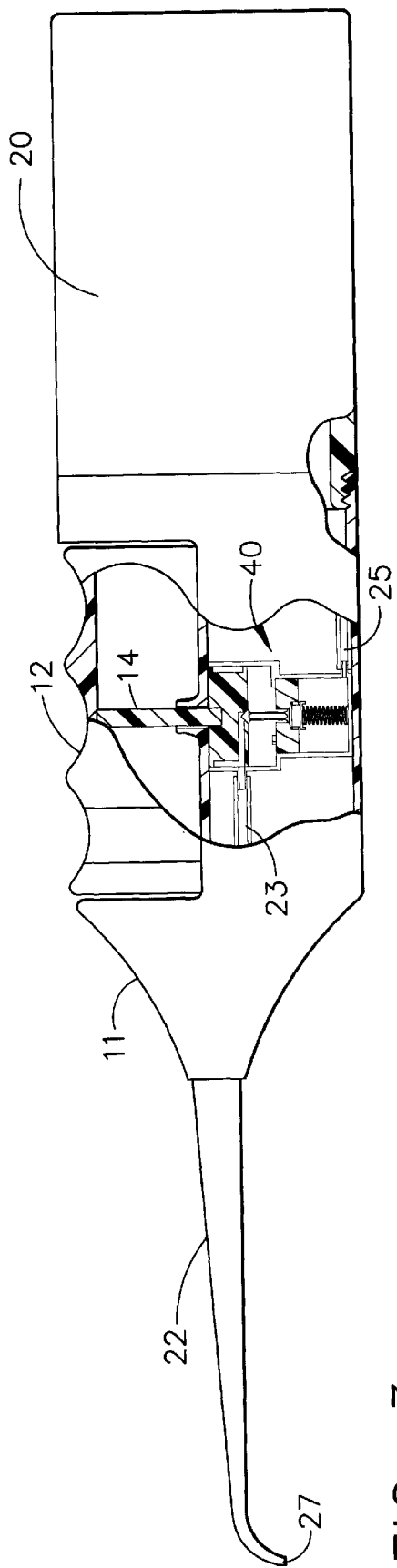
FIG. 3 is a side elevational view in a section of a second irrigator including a second hand-pump.

The hand held oral irrigation device of this invention will be described in detail with reference to the specific drawings. In these drawings, the different embodiments of the device have some common elements of construction. In order to simplify the description of these embodiments, like elements will have the same numeral identification for all embodiments.

FIG. 1 is an elevational view partially in section of one embodiment of the irrigator 10. A body housing 11 contains a hand grip 12 to actuate a hand-pump 13. A detachable section to the body housing is a reservoir 20 that contains the fluid that is to be dispensed. The reservoir 20 is attached to the body housing 11 with a threaded or other leak proof connector 21. In this first embodiment, a delivery section 22 is shown attached to the body housing 11. A first conduit 25 provides fluid connection between the reservoir 20 and the pump 13. A second conduit 23 provides fluid connection between the hand-pump 13 and the delivery section 22. The hand-pump 13, shown in cross-section in FIG. 2, is composed of a drive rod 14, a piston 15, a first spring 16, a cylinder 17, a ball check valve 18 and a pressure relief valve 19. A three or four finger grip 12 provides the means for activating the pump 13 through the drive rod 14. The grip 12 may be at least 2 in. (5.08 cm.) long to accommodate at least three fingers of the operator. For convenient operation by most persons, the grip 12 may be sized so that the user's fingers are opened less than 2 in. (5.08 cm.) in order to operate the hand-pump 13. Also the length of the irrigator 10 without the delivery section 22 may be approximately 8 inches (20.320 cm.) including the reservoir 20. A reservoir 20 having length of 4 inches (10.160 cm.) can hold approximately 12.2 cu. in. (200 cu. cm.) of fluid.

During operation, the hand grip 12 is depressed by the user and the piston 15 is forced into the cylinder 17, which decreases the volume and consequently increases the pressure therein. The pressure forces the ball check valve 18 to close and thereby prevent the fluid in the cylinder 17 from being forced back into the reservoir 20. The pressure of the fluid forces the pressure relief valve 19 against second spring 26 which allows the fluid to flow through the second conduit 23 to the delivery section 22 to be dispensed out of nozzle 27 illustrated in FIG. 1. A slot 24 in the drive rod 14 allows ambient air to enter the reservoir 20 during each stroke of the pump 13 in order to maintain the pressure therein substantially at the ambient value. When the grip 12 is depressed, the slot 24 provides an air connection to conduit 28 which connects to the air space in reservoir 20.

When the grip 12 is released, the spring 16 moves the piston 15 so as to increase the volume in the cylinder 17 and thereby decrease the pressure of the fluid therein. The atmospheric pressure in delivery section 22 and the second conduit 23 exceeds the pressure of the fluid in the cylinder 17 thereby, with the aid of the second spring 26, causing the relief valve 19 to close and prevent atmospheric air from entering cylinder 17. At this time the pressure in the reservoir 20 is approximately atmospheric and exceeds the pressure in the cylinder 17 thereby forcing the ball check valve 18 to open allowing liquid from the reservoir 20 to flow into the cylinder 17. When the piston 15 reaches the extended position against a housing surface 29 as a result of the force of the spring 16, the cycle can be repeated by squeezing grip 12 to cause the next fluid stream once again to be forced out of nozzle 27.

It will be instructive to determine the dimensions of the hand-pump 13 in order to provide the desired volume and pressure for each pulse of the discharged fluid stream. The following dimensions are exemplary. The volume of fluid that is discharged with each stroke of hand grip 12 is at least 0.040 cu. in. (0.655 cu. cm.), whereby the gauge pressure at the exit is at least 12 lb./sq. in. (8.273 newtons/sq.cm.), the force for depressing the hand grip 12 is less than 3.5 lb and, as discussed previously, the user's hand be opened less than 2 in. (5.08 cm.) to operate the hand grip 12. The fluid pressure at the exit nozzle 27 is controlled by the force of the second spring 26 in the relief valve 19. A convenient hand opening to operate the hand grip 12 is 1.750 in. (4.445 cm.). The body and the reservoir should also be 1.750 in. (4.445 cm.) in diameter. To contain the piston 15, the cylinder 17 and the first spring 16 within the body of a 1.750 in (4.445 cm.) diameter irrigator 10, limits the allowable stroke to be less than 0.470 in. (1.194 cm.). The strength of the first spring 16 is chosen as 1 lb. (4.448 newton) to provide sufficient force to return the piston 15 to the starting position. For example the cross-sectional area of the piston 15 is determined by the desired volume of the fluid that is dispensed at each stroke of the grip 12 and the length of the stroke. The cross-sectional area of the piston 15 equals the volume of fluid to be dispensed for each stroke of the grip 12 (0.040 cu. in.) divided by the length of the stroke of grip 12 (0.470 in.) or 0.085 sq. in. (0.549 sq. cm.). Thus the piston 15 has a diameter of 0.329 in (0.836 cm.). The force applied by the operator's fingers may be equal to the desired discharge pressure (12.000 lb./sq.in.) of the fluid times the cross-sectional area of the piston 15 (0.085 sq. in.) plus the spring force (1.000 lb.) or 2.020 lb. (8.985 newtons). In this example a force of less than the 3.5 lb. (15.568 newtons) would operate the hand-pump 13. A greater allowable finger force would permit a greater cross-sectional area for piston 15 and, for a given stroke, would result in a greater discharge volume of fluid. Alternately, a greater allowable finger force for a given piston area would result in a greater discharge pressure. An example of these two effects follows.

If a force for actuating the hand-pump 13 reaches 3.500 lb. (15.568 newtons), the cross-sectional area of piston 15 could be increased to 0.208 sq. in. (1.342 sq. cm.) in order to result in a finger force of 3.5 lb. (15.568 newtons) with a discharge pressure of 12 lb./sq.in. (8.273 newtons/sq. cm.) This larger cross-sectional area of the piston 15 would result in a greater volume of the discharge stream from 0.040 cu. in. (0.655 cu. cm.) to a value equal to the product of the cross-sectional area of the piston 15 (0.208 sq. in.) and the stroke (0.470 in.) or 0.098 cu. in. (1.602 cu. cm.).

Alternately, the pressure of the discharged fluid could be increased while keeping the volume of the stream constant at 0.040 cu. in. The discharge pressure of the fluid is determined by the allowable force to actuate the pump (3.5 lb.) minus the spring force (1 lb.) divided by the cross-sectional area of the piston 15 (0.085 sq. in.) or 29.412 lb./sq. in. (20.278 newtons/sq. cm.). The spring 26 in the relief valve 19 should provide sufficient force to cause the valve to remain closed until the gauge pressure of the fluid increases to the 29.412 lb./sq. in. (20.278 newtons/sq. cm.) as determined by the cross sectional area of the fluid flow passage for valve 19.

The hand-pump 13 could be contained in an irrigator 10 having a piston diameter of 0.329 in. (0.0836 cm.), stream volume of 0.04 cu. in., exit pressure of 12 lb./sq. in. (82.865 newtons/sq. cm.) with a finger force of 2.02 lb. (8.985 newton). Alternately, for the same body size with operating finger force of 3.5 lb. (15.568 newton), the discharge volume could be increased to 0.098 cu. in. (1.606 cu. cm.) or the discharge pressure could be increased to 29.412 lb./sq. in. (20.278 newtons/sq. cm.). ( Illustrating the strength of this pressure, theoretically it could produce vertical stream equal to 29.412/density of fluid =67.873 ft.)

The first embodiment of the hand-pump 13 will provide a stream of fluid at a relatively constant discharge pressure that is controlled by the second spring 26 in the relief valve 19. The first conduit 25 from reservoir 20 to hand pump 13 will supply fluid to the pump as long as the open end of conduit 25 is immersed in the fluid contained in reservoir 20. However, if the irrigator is held at an orientation such that the open end of the conduit 25 is not immersed in the fluid, the hand-pump 13 will not draw the fluid out of reservoir 20 and thereby will not dispense the fluid through nozzle 27. There are various known features that will deliver the fluid regardless of the orientation. For example U.S. Pat. No. 3,088,680 utilizes a flexible weighted end of the conduit that will fall by the force of gravity into the fluid contained in reservoir 20 thereby ensuring that the open end is always immersed in fluid. There are several other techniques to supply the fluid at most orientations that employ sliding cylinders or balls that move under the force of gravity either to open or close either the open end of the conduit or a second opening near the pump. An example of the ball feature is in U.S. Pat. No. 4,122,979. An example of a feature that does not require the force of gravity to function and has no moving parts is described in U.S. patent application Ser. No. 08/866,037 filed May 30, 1997 by one of the present inventors.

Figure 4:
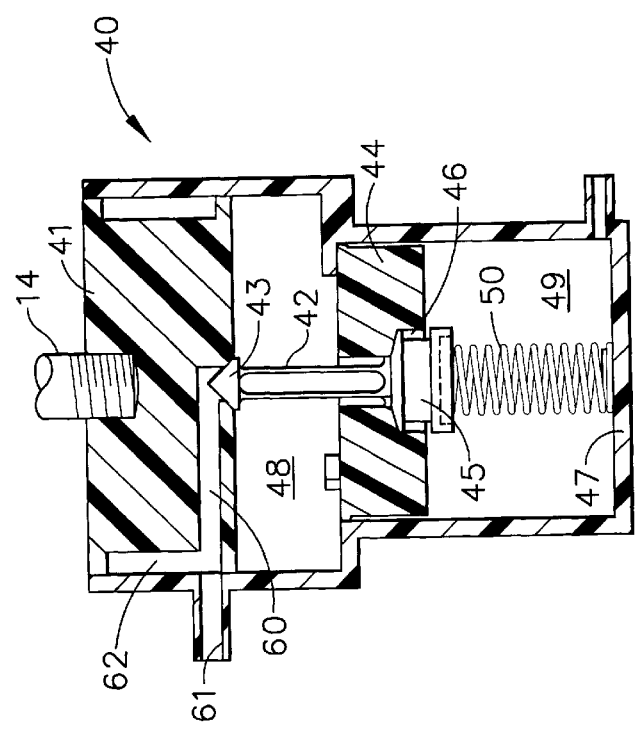
FIG. 4 is a sectional view of a hand-pump for the second irrigator.

A second irrigator of this invention has the same housing 11, reservoir 20, hand grip 12 and drive rod 14, but has a second hand-pump 40 in place of the first hand-pump 13 described above. FIG. 3 is a side elevational view in a section of the second irrigator. FIG. 4 is an enlarged cross-sectional view of hand-pump 40. A first (largest) cylindrical piston 41 is connected to the drive rod 14. A valve stem 42 forms a sealing surface 43 in cooperation with the first piston 41. The valve stem 42 is slideably mounted in a second (smaller) piston 44. A third (still smaller) cylindrical piston 45 located at one end of valve steam 42 is slideably mounted in cylinder 46 in the second piston 44. Housing 47 has a larger cross-sectional area 48 in which the first piston 41 is contained and a smaller circular cross-sectional area 49 in which the second piston 44 is contained. A spring 50 is contained between the base of the valve stem 42 and the base of housing 47.

FIG. 5 illustrates the operation of the second hand-pump 40. The second hand-pump 40 is illustrated in FIG. 5(a) in the nonoperating position. When the hand grip 12 in FIG. 3 is squeezed, drive rod 14 forces the first piston 41 further into the large area cylinder 48. As illustrated in FIG. 5b, this movement of the first piston 41 reduces the volume in cylinder 48 and causes an increase in the pressure of the fluid therein. The higher pressure overcomes the resistance of the spring 50 and forces the second piston 44 farther away from the first piston 41 into the smaller cylinder 49. The second piston 44 in turn moves the valve stem 42 away from the first piston 41 and allows fluid to flow into passage 60 in piston 41 and out of exit port 61. FIG. 5c illustrates that as the hand grip 12 is continued to be squeezed, the first piston 41 and the second piston 44 continue to be forced into their respective cylinders and fluid flows out of port 61 until the first piston 41 contacts a multitude of stops 63. The minimum discharge pressure remains constant during the entire stroke of the second hand-pump and the level of this pressure is controlled by the cross-sectional area of the second piston 44 and the force of the spring 50 against the valve stem 42.

Figure 5A:
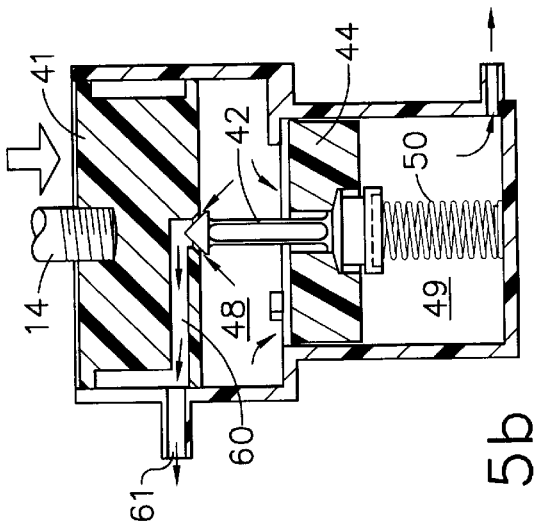
FIGS. 5(a) to 5(d) are sectional views illustrating the hand-pump shown in FIG. 4
Figure 5B:
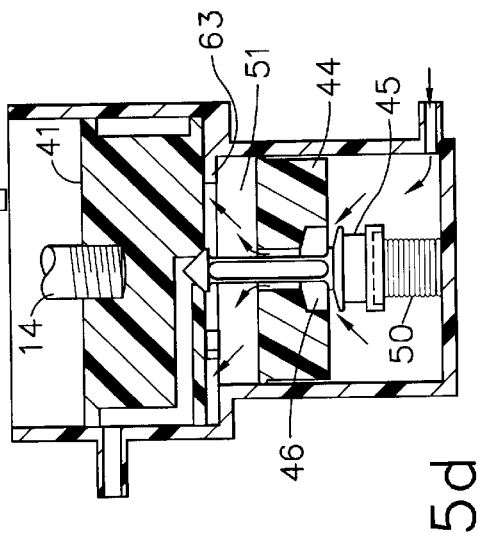
Figure 5C:
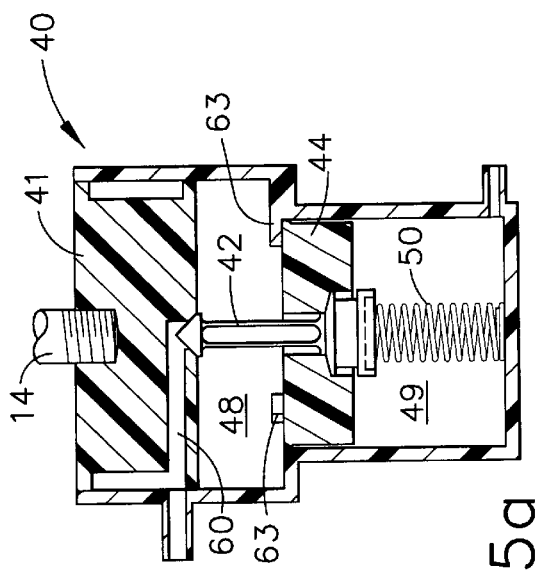
Figure 5D:
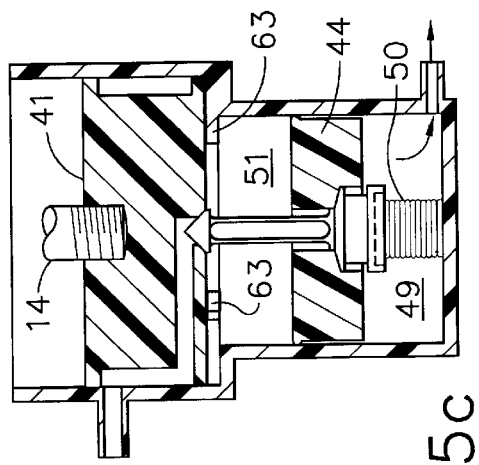

As illustrated in FIG. 5d, when the hand grip 12 is released, the spring 50 forces the valve stem 42 against the first piston 41 causing the volume 48 to increase. The pressure of the fluid within the volume contained between the first piston 41 and the second piston 44 consequently is lowered causing the second piston 44 to be forced off of the third piston 45 by the pressure from the fluid in the reservoir 20 and opening the passage 46 so that fluid can enter the cylinder volumes 48 and 51. This action also reduces the strength of the spring 50 that is required to return the first piston 41 and the second piston 44 to the starting position. The spring 50 continues to force the first piston 41 towards the starting position and the pressure difference across the second piston 44 continues to cause passage 46 to remain open until the second piston 44 reaches the stops 63. At this position, the cycle can repeat when the hand grip 12 shown in FIG. 1 again is squeezed.

The following exemplary dimensions of the second hand-pump 40 will obtain the same fluid discharge properties as the first hand-pump 13. A stroke of 0.300 in. (0.762 cm.) is the largest stroke that will allow the pump 40 to be installed in irrigator 10. The cross-sectional area of the first piston 41 equals the finger force (3.500 lb.) divided by the discharge pressure 12.000 lb./sq.in. or 0.292 sq. in (1.884 sq. cm.). To obtain this cross-sectional area, the diameter of the first piston 41 is 0.609 in. (1.547 cm.) If it is desired to have a fluid discharge volume of 0.040 cu. in. (0.655 cu. cm.) as in the case for the first hand-pump 13, the volume discharged from hand-pump 40 (0.04 cu.in.) is equal to the cross-sectional area of the first piston 41 (0.292 sq. in.) minus cross sectional area of second piston 44 times the stroke (0.300 sq. in.). As a consequence, the area of the second piston 44 is 0.159 sq. in. (1.026 sq. cm.) and the diameter is 0.450 in. (1.143 cm.). In order to produce a 12 lb./sq.in. gauge pressure before allowing the fluid to be discharged, the spring force equals the product of the discharge pressure (12 lb./sq. in.) and the cross-sectional area of the second piston (0.159 sq. in.) or 1.908 lb. (8.487 newton). To determine whether the force of 1.908 lb. is sufficient to force the first and second pistons 41 and 44 back to the starting position, the operation of the second hand-pump 40 is considered. When the spring 50 acts on the valve stem 42 to position the first piston 41 and the second piston 44 to the starting position, the fluid pressure between the first and second pistons 41 and 44 is decreased as a result of the increasing volume and results in a lower pressure than the atmospheric pressure which acts on the other sides of the first piston 41 and the second piston 44. The force acting against spring 50 resisting motion is equal to the difference between atmospheric pressure and the pressure of the fluid contained between the first piston 41 and the second piston 44 times the difference in the cross-sectional area of the two pistons. The pressure of the fluid between the second piston 44 and the first piston 41 is determined by the force that is required to lift the second piston 44 off of the valve stem 42 to allow liquid from the reservoir 20 to enter the volume between the first piston 41 and the second piston 44. Since the weight of the first piston 44 is small and the friction forces are small, the pressure between the first and second pistons 41 and 44 will be close to the atmospheric pressure. As a result, the spring force only needs to overcome the weight and friction forces of the first and second pistons and not overcome any significant force from the difference of pressure across the first and second pistons 41 and 44. As a result, the spring force of 1.908 lb. is sufficient. It is seen that the second hand-pump 40 will dispense 0.040 cu. in. (0.655 cu. cm.) with an exit gauge pressure of 12.000 lb./sq. in. (8.273 newton/sq. cm.) for an operating force of 3.5 lb. (15.568 newton) and that a spring force of approximately 1.908 lb (4.884 newton) will return the first and second pistons 41 and 44 to the starting position. The second hand-pump 40 will dispense fluid having the same properties as hand-pump 13 but with fewer parts, no separate valves and, consequently, be less expensive to manufacture.

Figure 6A:
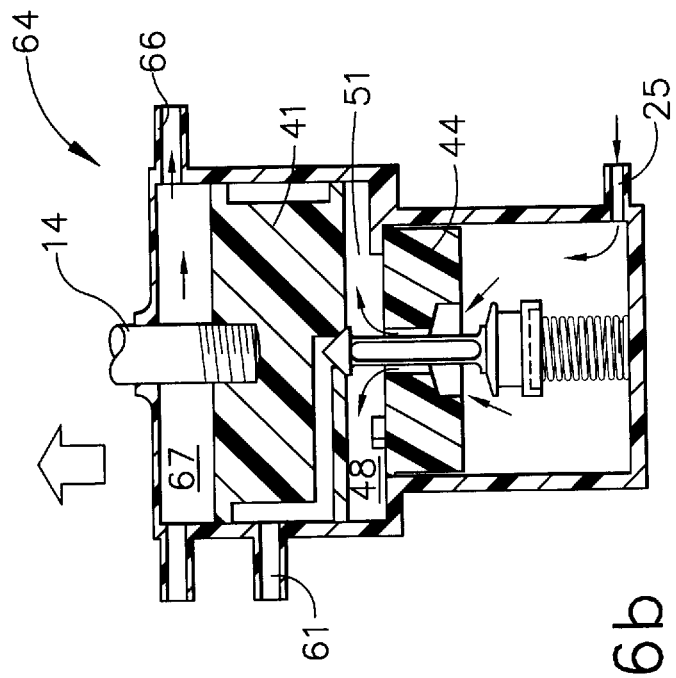
FIGS. 6(a) and 6(b) are cross-sectional views of a hand-pump for a third irrigator having both lavage and vacuum capabilities.
Figure 6B:
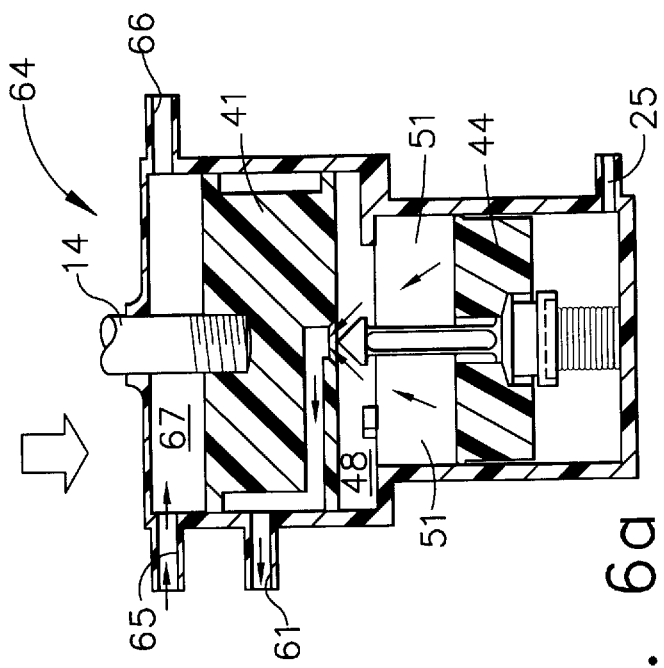

FIG. 6 illustrates an enlarged cross-sectional view of a third hand-pump 64 that is capable of ravaging as well as sucking the dispensed fluid into a conduit for convenient disposal. The third hand-pump 64 has the same components as the second hand-pump 40 illustrated in FIG. 4 The third hand-pump 64 has two additional ports: a suction port 65 and an exit port 66. The suction port 65 is in fluid communication with the suction inlet ports 83 which are positioned near the exit nozzle ports 81 as illustrated in FIG. 8 (b). In operation, during the normal pressure stroke of the third hand-pump 64 when the motion of the first piston 41 causes volume 48 to decrease and fluid is dispensed out of ports 81, volume 67 on the other side of piston 50 (which normally is not an active part) is increased thereby decreasing the pressure therein. The result is that fluid can be sucked through ports 83 of FIG. 8 (b) flowing through conduit 65 into volume 67 of FIG. 6 (a). During the normal suction stroke of the third hand-pump 64, when volume 48 is increased, volume 67 is decreased thereby increasing the pressure therein and consequently discharge the fluid contained within volume 67 through exit port 66 for convenient disposal. Suction port 65 has a conventional one way check valve, not shown, that allows fluid to enter cylinder 67 during the normal pressure stroke of the pump but not leave cylinder 67 during the normal suction stroke. Exit port 66 has a conventional one way check valve, not shown, to allow fluid to be released from volume 67 for disposal but not drawn in during the normal pressure stroke of the pump.

FIG. 7 illustrates in partial cross-section the third hand-pump 64 in the third irrigator 70. The fluid to be dispensed is contained in a bladder 68 and is drawn into the third hand-pump 64 through a conduit 25. The evacuated fluid from the user's mouth leaves the third hand-pump 64 through exit port 66 which is in fluid communication with the exterior of the bladder 68. In operation, the fresh fluid is drawn out of the interior of the bladder 68 for discharge to the person's mouth. The discharged fluid is drawn back into the third hand-pump 64 and passes through port 65 into conduit 69 and stored in the volume 71 around the exterior of the bladder 68. FIG. 8 (a) is a pictorial view of the tip of the third irrigator 70 including exit ports 81 in place of the single exit port 27 of FIG. 1. The discharged fluid flows into the periodontal pocket 82 between gum section 84 and tooth 85 and is drawn back into the discharge section 22 through suction ports 83 illustrated in FIG. 8 (b).

Hand-pump 13 or hand-pump 40 with added ports 65 and 66 would provide both a lavaging and vacuum capability in a single pump.

After completion of the irrigation, the reservoir 20 is unscrewed from the housing 11 and the bladder 68 can be refilled with fresh fluid. By opening valve 72, the evacuated fluid in the volume 71 can be removed with the aid of the force of gravity and the weight of fresh fluid that enters the bladder 68. Bladder 68 also allows irrigator to operate at any orientation.

As an alternate to storing the used fluid in the volume between the bladder 68 and the reservoir, the used fluid could be passed through.an extended conduit to a sink or other container for disposal.

Figure 9:
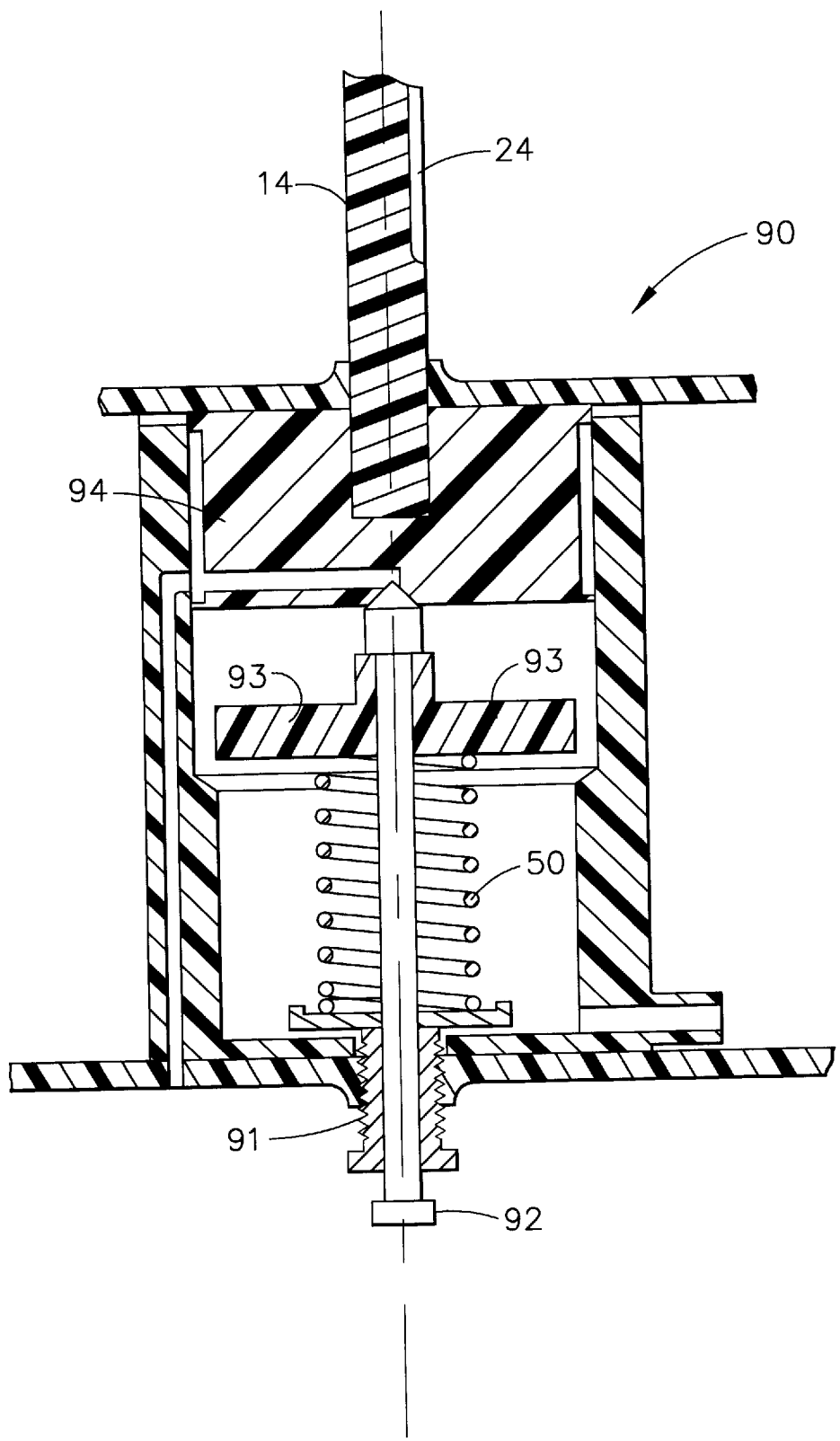
FIG. 9 illustrates the feature for adjusting the pressure and the volume of the discharge fluid from a fourth hand-pump.

FIG. 9 illustrates in cross-section a fourth hand-pump 90 having the capability of adjusting both the discharge pressure of the fluid and the volume of the fluid that is discharge during each stroke of the fourth hand-pump 90. A screw device 91 allows the spring 50 to be shortened thereby increasing the force on piston 93 and increasing the discharge pressure of the fluid. The screw device 92 positions the smaller piston 93 relative to the larger piston 94 and could reduce the stroke thereby decreasing the volume of fluid that is dispensed during each stroke of the fourth hand-pump 90.

FIG. 10 illustrates an irrigator in which the irrigator section 22 is replaced with a toothbrush 101. Irrigator section 22 and other attachments are connected to the body 12 by conventional liquid connectors such as a Luhr lock. The toothbrush 101 includes a handle 102 having a conduit 103 for passing fluid from the hand-pump to the head 104 of the toothbrush 101. The head 104 has a multitude of exit ports 111 between the rows of bristles 112 that provides fluid to the user's oral cavity. Three rows of bristles and at least four exit ports may be spaced longitudinally between the two outer rows of bristles. FIG. 11 shows three rows of bristles 111 and six exit ports 112 in the head of the toothbrush 101 to allow the fluid to be dispensed into the user's mouth.

FIG. 12 illustrates an irrigator in which the irrigator section 22 is replaced with a plaque removal brush 121 installed longitudinally with the irrigator 10. The plaque removal brush 121 should have bristles 122 of varying length so as to form a cone. This irrigator allows the brush 121 to be inserted between teeth. The Proxabrush manufactured by J. L. Butler Co. in Chicago, Ill. is typical of the conical configuration. Liquid from the reservoir 20 can be injected into the user's mouth through conduit 123 and out of a multitude of exit ports 124 to aid in the removal of the plaque. One or more exit ports can supply sufficient fluid. FIG. 12 illustrates the configuration with four exit ports 124.

FIG. 13(a) illustrates the plaque removal brush 131 installed at right angles to the irrigator for easier operation by the user.

FIG. 13(b) illustrates the plaque removal brush with a simple liquid screw device 132 that causes the brush 121 to rotate when driven by the fluid from reservoir 20 when the hand grip 12 is activated. Fluid from the hand-pump is forced to flow through conduit 133 and between the screw-type threads of device 132 to cause the shaft 134 to rotate. In this irrigator, the exit port 135 for the fluid is formed between the rotatable shaft 134 and the housing 135 for the screw device 132.

FIG. 13(c) illustrates the plaque removal brush 121 with a liquid turbine 136 that causes the brush 121 to rotate when driven by the fluid from reservoir 20 when the grip 12 is activated. In this case the fluid from the hand-pump enters the fluid turbine 136 through conduit 137. The exit port 138 is formed by the annular space between the rotatable shaft and the turbine housing 140.

FIG. 14 illustrates a gum massaging tip 141 installed in the irrigator 10. The tip 141 is fabricated of rubber so as to allow stimulation without injuring the gum. There is a fluid conduit (not shown) from the hand-pump to the tip 141 so that fluid can be injected out of the tip 141 while the gum area is being stimulated. It is then possible simultaneously to cleanse the area that is being stimulated. FIG. 15 is an enlarged side view and FIG. 16 is an enlarged end view of the massaging tip unit 141. Six exit ports for the fluid are shown. Fluid from the hand-pump is dispensed out of exit ports 142 and flows through conduits 143 that are formed between the massage unit surface and the user's gum or tooth surface to the tip of the massage unit 141 and then through conduits 144 that are formed between the massage unit surface and the user's gum or tooth surface. The fluid removes any material in the area when it flows from the exit port 142 to the tip of the massage unit 141 as well as when it flows from the tip out of the massage to unit.

The arrangements described herein are merely illustrative applications of the principles of the invention. Numerous modifications will readily occur to those skilled in the art without departing from the spirit and scope of the invention. These changes are contemplated by and are within the scope of the appending claims which define the present invention.

What is claimed is:

1. A hand-held oral irrigation device comprising:
   a fluid reservoir;
   a longitudinally-spaced fluid discharge section,
   an actuator movable between depressed and extended positions;
   a longitudinally-spaced hand pump responsive to the actuator; and
   a longitudinally-spaced body surroundings the hand pump:
   a fluid reservoir and the fluid discharge section extending from opposite sides of the body:
   the actuator extending to about a perimeter of the body when the actuator is in the extended position.

2. The device of claim 1, wherein the actuator is finger-operable.

3. The device of claim 1, wherein the actuator includes a push rod and a handle secured to a first end of the push rod, a second end of the push rod being coupled to the pump.

4. The device of claim 3, wherein the handle is configured to be grasped by multiple fingers.

5. The device of claim 1, wherein the pump includes a piston movable within a chamber, and a cooperating spring mechanically coupled to the actuator; the fluid pressure in a volume defined by the piston and a chamber base being increased by the movement of the piston by finger force on the actuator during a first stroke of the actuator and reduced by the motion of the piston by the spring force during a second stroke of the actuator; wherein the means further includes a first valve disposed in a fluid passage between a chamber outlet and a volume within the chamber and a second valve disposed in a fluid passage between a chamber inlet and the volume; the increased fluid pressure in the volume during the first stroke causing the second valve to close and the first valve to open and place the chamber outlet in fluid communication with the volume, whereby the fluid pressure in the volume causes fluid in the volume to be discharged through the chamber outlet to the fluid discharge section; the reduced fluid pressure in the volume during the second stroke causing the first valve to close and the second valve to open and place the chamber inlet in fluid communication with the volume, whereby the reduced fluid pressure in the volume causes fluid from the reservoir to be drawn into the volume.

6. The device of claim 5, further comprising a fluid reservoir wherein said chamber inlet is in fluid communication with a conduit extending into the fluid contained in the reservoir, said conduit being open at a free end.

7. The device of claim 5, wherein said fluid discharge section is terminated with a multitude of jetting ports.

8. The device of claim 1, wherein the pump includes first and second pistons movable within a chamber, the first piston being mechanically coupled to the actuator, the first and second pistons defining a first volume, the volume being pressurized by the movement of the first and second pistons during a first stroke of the actuator, the pump further including a valve disposed in a fluid passage between a chamber outlet and the volume, the pressure of the fluid in the volume causing the valve to open and place the chamber outlet in fluid communication with the volume, wherein fluid pressure can cause fluid in the volume to be discharged through the chamber outlet to the fluid discharge section.

9. The device of claim 1, further comprising a collapsible bladder inside the fluid reservoir, whereby an interior of the bladder is in fluid communication an inlet port of the pump.

10. The device of claim 1, wherein the fluid discharge section includes a toothbrush having fluid passage from said means to a head of said toothbrush, said toothbrush head having multiple rows of bristles and a multitude of fluid exit ports located between the bristles.

11. The device of claim 1, wherein said fluid discharge section includes a plaque removal brush having fluid exit passage connecting from said pump to said brush.

12. The device of claim 1, wherein said fluid discharge section includes a plaque removal brush having fluid exit passage and suction passage in fluid communication with said pump.

13. The device of claim 12, wherein said discharge section includes a plaque removal brush that is rotatably mounted to a fluid turbine that is driven by fluid from the pump.

14. The device of claim 1, wherein said discharge section includes a gum stimulator having a body and a multitude of exit jetting ports having cooperating channels for directing the dispensed fluid towards a smaller tip end into a gum periodontal pocket and then out of the pocket towards a larger end of the stimulator body.

15. The device of claim 14, wherein a volume is defined within the pump and a suction port is in fluid communication with the volume during a first stroke of the actuator, and wherein said gum stimulator further has the smaller tip end being in fluid communication with an outlet port of the pump and a larger end being in fluid communication with the suction port.

16. A hand-held oral irrigation device comprising:
   a fluid discharge section;
   an actuator movable in first and second strokes; and
   a hand pump including:
   a fluid chamber having an inlet and an outlet, the chamber outlet being in fluid communication with the fluid discharge section; and
   first and second pistons movable within the chamber, the first piston being mechanically coupled to the actuator, the first and second pistons defining a first volume within the chamber, the first volume being pressurized by the movement of the first and second pistons during the first stroke; and
   a valve disposed in a fluid passage between the chamber outlet and the first volume, pressure in the first volume causing the valve to open and place the chamber in fluid communication with the first volume, whereby the pressure can cause fluid in the first volume to be discharged through the chamber outlet to the fluid discharge section.

17. The device of claim 16, further comprising a body and a fluid reservoir, the pump being secured to the body, the fluid discharge section being longitudinally detachable from the body and the reservoir being longitudinally detachable from the body, to the fluid discharge section and reservoir being attachable to opposite sides of the body.

18. The device of claim 16, wherein the fluid discharge section is terminated with a multitude of exit jetting ports.

19. The device of claim 18, further comprising fluid jetting ports secured to said discharge section, a body of each port being tapered from a larger diameter end adjacent to said discharge section to a narrower end, whereby fluid can be emitted from one or more said jetting ports near said narrower end into channels formed circumferentially about and with said body and extending longitudinally thereof, said larger end having one or more suction ports therein disposed about its periphery to draw used fluid into hand-pump for disposal.

20. The device of claim 16, wherein the second piston and a chamber base define a second volume, the second volume being in fluid communication with the chamber inlet, and wherein the pump includes a second valve disposed in a fluid passage between the first and second volumes, the second valve being closed during the first stroke wherein the fluid in the first volume is pressurized, the first and second pistons creating suction during the second stroke, the suction causing the second valve to open, whereby the suction can cause fluid to be drawn through the chamber inlet into the second volume and then through the second valve into the first volume.

21. The device of claim 20, further comprising a fluid reservoir wherein said chamber inlet is in fluid communication with a conduit extending into the reservoir, the conduit being open at a free end.

22. The device of claim 20, wherein the second piston includes a bore, and wherein the second valve includes a third piston movable in and out of the bore.

23. The device of claim 22, wherein the first valve has a conical sealing surface with the flow passage in the first piston being longitudinally connected to the second valve, the first valve being positioned by a spring located between the base of the chamber and the base of the third piston.

24. The device of claim 23, wherein the second piston engages the third piston during the first stroke to open the first valve and wherein the second piston moves away from the third piston during the second stroke to open the second valve.

25. The device of claim 24, wherein the first piston has a larger diameter than the second piston, wherein the first and second pistons both have mating chambers.

26. The device of claim 16, wherein the chamber further has a suction port, and wherein the first piston and a chamber top define a third volume, the third volume being in fluid communication with a suction port during the first stroke, whereby the first piston evacuates the third volume and pressurizes the first volume causing a first fluid to be discharged from the first volume and out of the discharge section and a second fluid can be drawn into the third volume through the suction port.

27. The device of claim 26, further comprising fluid jetting ports fluidly secured to said discharge section, a body of each port being tapered from a larger diameter end adjacent to said discharge section to a narrower end, whereby fluid can be emitted from one or more said exit jetting ports near said narrower end into channels formed circumferentially about and with said body and extending longitudinally thereof, said larger end having one or more suction ports therein disposed about its periphery to draw used fluid into hand-pump for disposal.

28. The device of claim 26, wherein the chamber further has a discharge port in fluid communication with the third volume during the second stroke, whereby fluid is discharged from the third volume through the discharge port.

29. The device of claim 28, further comprising a conduit in fluid communication with the third volume, the conduit being adapted to dispose used fluid external to the device.

30. The device of claim 28, wherein the means further includes a third valve in fluid communication with the suction port, and a fourth valve in fluid communication with the discharge port.

31. The device of claim 30, further comprising a fluid reservoir and a bladder within the reservoir, wherein the reservoir and the exterior surface of the bladder defining a fourth volume, the fourth volume being in fluid communication with the discharge port.

32. A hand-held oral irrigation device comprising:
   a fluid discharge section including a plaque removal brush, the plaque removal brush having a fluid exit passage and a suction passage;
   an actuator movable in first and second strokes; and
   a hand pump including
   a fluid chamber having an inlet and an outlet, the chamber outlet being in fluid communication with the fluid discharge section; and
   means, responsive to the actuator, for simultaneously pressurizing the fluid chamber, closing the chamber inlet and opening the chamber outlet during the first stroke of the actuator, the means simultaneously creating suction in the fluid chamber, opening the chamber inlet and closing the chamber outlet during the second stroke of the actuator;
   the fluid exit and suction passages of the plaque removal brush being connectable to the means.

33. The device of claim 32, wherein the plaque removal brush is rotatably mounted to a fluid turbine that is driven by fluid from the pump.

34. A hand-held oral irrigation device comprising:
   a fluid discharge section including a gum stimulator, the gum stimulator having a body, a multitude of exit jetting ports and first and second tip ends;
   an actuator movable in first and second strokes; and
   a hand pump including:
   a fluid chamber having an inlet and an outlet, the chamber outlet being in fluid communication with the fluid discharge section; and
   means, responsive to the actuator, for simultaneously pressurizing the fluid chamber, closing the chamber inlet and opening the chamber outlet during the first stroke of the actuator, the means simultaneously creating suction in the fluid chamber, opening the chamber inlet and closing the chamber outlet during the second stroke of the actuator;
   the chamber having a volume defined by the means and a chamber wall, the chamber further having a suction pod in fluid communication with the volume during the first stroke;
   the first tip end of the gum stimulator being in fluid communication with the outlet port and the second end of the gum stimulator being in fluid communication with the suction port.

* * * * *